(12) United States Patent
Gyurik et al.

(10) Patent No.: US 7,112,561 B2
(45) Date of Patent: Sep. 26, 2006

(54) PHARMACEUTICAL COMPOSITIONS AND METHODS FOR INSULIN TREATMENT

(75) Inventors: Robert J. Gyurik, Exeter, NH (US); Carl Reppucci, North Andover, MA (US)

(73) Assignee: Bentley Pharmaceuticals, Inc., Exeter, NH (US)

( * ) Notice: Subject to any disclaimer, the term of this patent is extended or adjusted under 35 U.S.C. 154(b) by 0 days.

(21) Appl. No.: 11/002,858

(22) Filed: Dec. 2, 2004

(65) Prior Publication Data
US 2005/0123592 A1 Jun. 9, 2005

Related U.S. Application Data

(60) Provisional application No. 60/527,728, filed on Dec. 8, 2003.

(51) Int. Cl.
*A61K 38/00* (2006.01)
(52) U.S. Cl. .................................................. 514/3
(58) Field of Classification Search ............ 514/3
See application file for complete search history.

(56) References Cited

U.S. PATENT DOCUMENTS

| | | | |
|---|---|---|---|
| 4,211,766 A | 7/1980 | Bjorklund | 424/277.1 |
| 4,603,120 A | 7/1986 | Kamber | 514/11 |
| 4,613,500 A | 9/1986 | Suzuki et al. | 429/85 |
| 4,755,534 A | 7/1988 | Stuetz | 514/655 |
| 4,760,096 A | 7/1988 | Sakai et al. | 514/847 |
| 4,894,375 A | 1/1990 | Gadebusch et al. | 514/249 |
| 4,920,109 A | 4/1990 | Onishi et al. | 514/171 |
| 4,920,112 A | 4/1990 | Onishi et al. | 514/171 |
| 4,957,730 A | 9/1990 | Bohn et al. | 424/61 |
| 4,983,393 A | 1/1991 | Cohen et al. | 424/430 |
| 5,023,252 A | 6/1991 | Hseih | 514/183 |
| 5,028,431 A | 7/1991 | Franz et al. | 424/449 |
| 5,057,312 A | 10/1991 | Langla et al. | 424/81 |
| 5,069,906 A | 12/1991 | Cohen et al. | 424/430 |
| 5,106,878 A | 4/1992 | Guerry et al. | 514/651 |
| 5,116,603 A | 5/1992 | Friedman | 424/53 |
| 5,120,530 A | 6/1992 | Ferro et al. | 424/61 |
| 5,132,459 A | 7/1992 | Stuetz | 564/387 |
| 5,160,737 A | 11/1992 | Friedman et al. | 424/401 |
| 5,179,079 A | 1/1993 | Hansen et al. | 514/4 |
| 5,214,046 A | 5/1993 | Guerry et al. | 514/255 |
| 5,262,150 A | 11/1993 | Laugier et al. | 424/47 |
| 5,437,272 A | 8/1995 | Fuhrman | 128/203.12 |
| 5,490,498 A | 2/1996 | Faithfull et al. | 128/203.12 |
| 5,514,670 A | 5/1996 | Friedman et al. | 514/2 |
| 5,540,225 A | 7/1996 | Schutt | 128/207.15 |
| 5,562,608 A | 10/1996 | Sekins et al. | 604/20 |
| 5,614,171 A | 3/1997 | Clavenna et al. | 424/45 |
| 5,618,516 A | 4/1997 | Clavenna et al. | 424/45 |
| 5,660,839 A | 8/1997 | Allec et al. | 424/401 |
| 5,661,170 A | 8/1997 | Chodosh | 514/390 |
| 5,667,809 A | 9/1997 | Trevino et al. | 424/501 |
| 5,681,849 A | 10/1997 | Richter et al. | 514/481 |
| 5,696,164 A | 12/1997 | Sun et al. | 514/562 |
| 5,719,192 A | 2/1998 | De Simone et al. | 514/655 |
| 5,731,303 A * | 3/1998 | Hsieh | 514/183 |
| 5,733,877 A | 3/1998 | Sato et al. | 514/12 |
| 5,807,890 A | 9/1998 | Yu et al. | 514/574 |
| 5,813,416 A | 9/1998 | Rudolph | 132/76.4 |
| 5,814,305 A | 9/1998 | Laugier et al. | 424/61 |
| 5,817,875 A | 10/1998 | Karimian et al. | 564/387 |
| 5,837,289 A | 11/1998 | Grasela et al. | 424/484 |
| 5,840,283 A | 11/1998 | Sorenson et al. | 424/61 |
| 5,856,355 A | 1/1999 | Richter et al. | 514/481 |
| 5,866,105 A | 2/1999 | Richter et al. | 424/61 |
| 5,898,028 A * | 4/1999 | Jensen et al. | 514/4 |
| 5,902,789 A | 5/1999 | Stoltz | 514/4 |
| 5,908,824 A | 6/1999 | Yanagawa | 514/2 |
| 5,925,616 A | 7/1999 | Whittemore | 514/2 |
| 5,935,998 A | 8/1999 | Lindley et al. | 514/481 |
| 5,942,545 A | 8/1999 | Samour et al. | 514/573 |
| 5,945,409 A | 8/1999 | Crandall | 514/78 |
| 5,968,919 A | 10/1999 | Samour et al. | 514/177 |
| 5,976,547 A | 11/1999 | Archer et al. | 424/742 |
| 5,976,566 A | 11/1999 | Samour et al. | 424/449 |
| 5,985,906 A | 11/1999 | Meingassner et al. | 514/383 |
| 5,993,787 A | 11/1999 | Sun et al. | 424/59 |
| 6,005,001 A | 12/1999 | Richter et al. | 514/481 |
| 6,017,920 A | 1/2000 | Kamishita et al. | 514/252 |
| 6,024,976 A | 2/2000 | Miranda et al. | 424/449 |
| 6,030,948 A | 2/2000 | Mann | 514/12 |
| 6,121,314 A | 9/2000 | Richter et al. | 514/481 |
| 6,136,332 A | 10/2000 | Grollier et al. | 424/404 |

(Continued)

FOREIGN PATENT DOCUMENTS

EP 0156507 10/1985

(Continued)

OTHER PUBLICATIONS

Aungst et al., Site Dependence of Absorption-Promoting Actions of Laureth-9, Na Salicylate, Na₂EDTA, and Aprotinin on Rectal, Nasal, and Buccal Insulin Delivery, Pharmaceutical Research, vol. 5, No. 5, pp. 305-308, Jan 2, 1988.

(Continued)

*Primary Examiner*—Cecilia J. Tsang
*Assistant Examiner*—Maury Audet
(74) *Attorney, Agent, or Firm*—Elliot M. Olstein; Raymond E. Stauffer (57) ABSTRACT

Compositions and methods for treating a patient with insulin that combines insulin, a permeation enhancer, and a carrier that maintains an acidic pH, are disclosed.

66 Claims, 2 Drawing Sheets

U.S. PATENT DOCUMENTS

| | | | |
|---|---|---|---|
| 6,142,155 A | 11/2000 | Rudolph | 132/76.4 |
| 6,143,793 A | 11/2000 | Laugier et al. | 514/655 |
| 6,165,484 A | 12/2000 | Raad et al. | 424/405 |
| 6,190,690 B1 | 2/2001 | Park et al. | 424/449 |
| 6,207,142 B1 | 3/2001 | Odds et al. | 424/70.8 |
| 6,207,703 B1 | 3/2001 | Ponikau | 514/460 |
| 6,214,360 B1 | 4/2001 | Richter et al. | 424/401 |
| 6,221,383 B1 | 4/2001 | Miranda et al. | 424/449 |
| 6,224,887 B1 | 5/2001 | Samour et al. | 424/401 |
| 6,225,075 B1 | 5/2001 | Bard | 435/15 |
| 6,231,875 B1 | 5/2001 | Sun et al. | 424/401 |
| 6,242,509 B1 | 6/2001 | Berger et al. | 523/122 |
| 6,267,979 B1 | 7/2001 | Raad et al. | 424/405 |
| 6,291,500 B1 | 9/2001 | Ponikau | 514/393 |
| 6,294,192 B1 | 9/2001 | Patel et al. | 424/451 |
| 6,294,350 B1 | 9/2001 | Peterson | 435/29 |
| 6,319,509 B1 | 11/2001 | Richter et al. | 424/401 |
| 6,328,728 B1 | 12/2001 | Holladay et al. | 604/501 |
| 6,335,023 B1 | 1/2002 | Yu et al. | 424/401 |
| 6,380,236 B1 | 4/2002 | Glassman | 514/399 |
| 6,383,471 B1 | 5/2002 | Chen et al. | 424/45 |
| 6,383,523 B1 | 5/2002 | Murad | 424/616 |
| 6,399,571 B1 | 6/2002 | Gray et al. | 514/12 |
| 6,403,063 B1 | 6/2002 | Sawyer | 424/61 |
| 6,433,040 B1 | 8/2002 | Dellamary et al. | 523/218 |
| 6,455,592 B1 | 9/2002 | Laugier et al. | 514/655 |
| 6,479,532 B1 | 11/2002 | Kamimura et al. | 514/397 |
| 6,482,839 B1 | 11/2002 | Thornfeldt | 514/345 |
| 6,485,706 B1 | 11/2002 | McCoy et al. | 424/45 |
| 6,495,124 B1 | 12/2002 | Samour | 424/61 |
| 6,503,953 B1 | 1/2003 | Vyden | 514/741 |
| 6,509,319 B1 | 1/2003 | Raad et al. | 514/31 |
| 6,514,490 B1 | 2/2003 | Odds et al. | 424/70.8 |
| 6,515,181 B1 | 2/2003 | Castaldi et al. | 564/387 |
| 6,531,126 B1 | 3/2003 | Farmer | 424/115 |
| 6,555,566 B1 | 4/2003 | Ponikau | 514/393 |
| 6,569,463 B1 | 5/2003 | Patel et al. | 424/497 |
| 6,585,967 B1 | 7/2003 | Narang et al. | 424/78.31 |
| 6,596,325 B1 | 7/2003 | Vroom | 424/769 |
| 6,602,496 B1 | 8/2003 | Hedgpeth et al. | 424/78.07 |
| 6,604,698 B1 | 8/2003 | Verhoff et al. | 241/21 |
| 6,623,732 B1 | 9/2003 | Ma | 424/85.4 |
| 6,623,753 B1 | 9/2003 | Bodmer et al. | 424/450 |
| 6,645,506 B1 | 11/2003 | Farmer | 424/260.1 |
| 6,645,528 B1 | 11/2003 | Straub et al. | 424/489 |
| 6,673,054 B1 | 1/2004 | Gould et al. | 604/292 |
| 6,673,369 B1 | 1/2004 | Rampal et al. | 424/468 |
| 6,680,308 B1 | 1/2004 | Hassan | 514/125 |
| 6,688,304 B1 | 2/2004 | Gonda et al. | 128/200.14 |
| 6,689,913 B1 | 2/2004 | Lee et al. | 564/337 |
| 6,689,986 B1 | 2/2004 | Patel et al. | 219/121.71 |
| 6,694,975 B1 | 2/2004 | Schuster et al. | 128/203.26 |
| 6,849,263 B1 | 2/2005 | Modi | 424/400 |
| 6,878,365 B1 | 4/2005 | Brehove | 424/61 |
| 6,899,890 B1 | 5/2005 | Kirschner et al. | 424/430 |
| 6,914,051 B1 | 7/2005 | Allen | 514/29 |
| 6,956,058 B1 * | 10/2005 | Hase et al. | 514/547 |
| 6,967,192 B1 | 11/2005 | Oeltgen et al. | 514/12 |
| 2001/0055569 A1 | 12/2001 | Davis et al. | 424/43 |
| 2002/0123437 A1 * | 9/2002 | Conboy et al. | 510/101 |
| 2002/0165155 A1 | 11/2002 | Schaffer et al. | 514/12 |
| 2003/0049307 A1 | 3/2003 | Gyurik | 424/449 |
| 2003/0086881 A1 | 5/2003 | Bohn et al. | 424/61 |
| 2003/0188679 A1 | 10/2003 | Schwarz et al. | 117/2 |
| 2003/0211995 A1 | 11/2003 | Kokai-Kun et al. | 514/12 |
| 2003/0229010 A1 | 12/2003 | Ekwuribe | 514/3 |
| 2004/0167203 A1 | 8/2004 | Chang et al. | 514/440 |
| 2004/0176476 A1 | 9/2004 | Gyurik | 514/772.6 |
| 2004/0197280 A1 | 10/2004 | Repka | 424/61 |
| 2004/0235956 A1 | 11/2004 | Quay | 514/573 |
| 2005/0032683 A1 | 2/2005 | Amento et al. | 514/12 |
| 2005/0069578 A1 | 3/2005 | Balasubramanian | 424/450 |
| 2005/0215477 A1 | 9/2005 | Schaffer et al. | 514/12 |

FOREIGN PATENT DOCUMENTS

| | | |
|---|---|---|
| EP | 0226984 | 7/1987 |
| EP | 0298271 | 1/1989 |
| EP | 0325949 | 8/1989 |
| EP | 0385952 | 9/1990 |
| EP | 0399858 | 11/1990 |
| EP | 0472858 | 3/1992 |
| EP | 0478456 | 4/1992 |
| EP | 0503988 | 9/1992 |
| FR | 2265357 | 10/1975 |
| GB | 2002795 | 2/1979 |
| GB | 2098865 | 12/1982 |
| GB | 2148711 | 6/1985 |
| GB | 2197194 | 5/1988 |
| WO | WO 87/02580 | 5/1987 |
| WO | WO 88/06884 | 9/1988 |
| WO | WO 96/35423 | 11/1996 |
| WO | WO 97/02026 | 1/1997 |
| WO | WO 99/59543 | 11/1999 |
| WO | WO 03/000158 | 1/2003 |
| WO | WO 03/088974 | 10/2003 |
| WO | WO 05/056038 | 6/2005 |

OTHER PUBLICATIONS

Gallo et al., Allergic Contact Dermatitis From Laureth-9 and Polyquatemium-7 in a Skin-Care Product, Contact Dermatitis, vol. 45, No. 6, Dec. 2001.

Jones, Treatment of Dermatomycoses with Topically Applied Allylamines: Naftifine and Terbinafine, Journal of Dermatological Treatment, 1990, pp. 29-32.

Kokai-Kun et al., Lysostaphin Cream Eradicates Staphylococcus Aureus Nasal Colonization in a Cotton Rat Model, Antimicrob Agents Chemother. May 2003; 47(5): 1589-97.

Leary et al., Pharmacokinetics and Pharmacodynamics of Intranasal Insulin Administered to Healthy Subjects in Escalating Doses, Diabetes Technol. Ther. Feb. 2005;7(1):124-30 (Abstract).

Leary et al., Pharmacokinetics and Pharmacodynamics of Intranasal Insulin Administered to Patients with Type 1 Diabetes: A Preliminary Study, Diabetes Technology & Therapeutics vol. 8, No. 1, 2006.

Leary et al., Intranasal Insulin Administration in Normal Subjects Utilizing CPE-215® Technology, (Abstract No. Lear 4167 and Poster), Diabetes Technology Meeting in Philadelphia, PA, Oct. 28-30, 2004.

Leary et al., Intranasal Insulin Administration in Type I Diabetic Patients Utilizing CPE-215® Technology, (Abstract No. Lear 952997 and Poster), American Diabetes Association Meeting in San Diego, CA, Jun. 9-14, 2005.

Lochhead et al., Hydrophobically Modified "Carbopol" Resins, Soap/Cosmetics/Chemical Specialities for May 1987, pp. 28-33.

Mort, Multiple Modes of Drug Delivery, Technologies such as microchips and microspheres and enabling the therapeutic use of proteins, Modern Drug Discovery, Apr. 2000, 3(3) 30-32, 34.

Patton, Deep-Lung Delivery of Therapeutic Proteins, Chemtech, Dec. 1997, Chemtech 1997, 27(12), 34-38.

Paulsen, Contact Sensitization From Compositae-Containing Herbal Remedies and Cosmetics, Contact Dermatitis, Oct. 2002;47(4): 189-98.

Petranyl et al., Activity of Terbinafine in Experimental Fungal Infections of Laboratory Animals, Antimicrobial Agents and Chemotherapy, Oct. 1987, p. 1558-1561.

Savin, Successful Treatment of Chronic Tinea Pedis (moccasin type) With Terbinafine (Lamisil), Clinical and Experimental Dermatology 1989; 14: 116-119.

Spettoli et al., Contact Dermatitis Caused by Sesquiterpene Lactones, Am J Contact Dermat. Mar. 1998; 9(1): 49-50.

Taylor et al., Structural Studies of Phycobiliproteins From Spiruiina: Combining Spectroscopy, Thermodynamics, and Molecular Modeling in an Undergraduate Biochemisty Experiment, Journal of Chemical Education, vol. 79, No. 12, pp. 1467-1470, Dec. 2002.

Villars et al., Present Status of the Efficacy and Tolerability of Terbinafine (Lamisil) Used Systemically in the Treatment of Dermatomycoses of Skin and Nails, Journal of Dermatological Treatment (1990), 1, Suppl. 2, 33-38.

Willimann et al., Lecithin Organogel as Matrix for Transdermal Transport of Drugs, Journal of Pharmaceutical Sciences, vol. 81, No. 9, pp. 871-874, Sep. 1992.

Young et al., Histoplasmosis and HIV Infection, HIV InSite Knowledge Base Chapter, May 2005.

About MEROPS, Classification: Three Orthogonal Approaches.

Ammonlum Thioglycolate Haz Map, Occupational Exposure to Hazardous Agents.

Bachem AG, Myelin Basic Protein Fragments, H-2680, H-3584, H-1072, H-3238, H-6870, H-6875, H-4306, H-1964, H-3392, H-6022 and Peptides H-9435, H-5806, H-3046, H-2155, H-3914, H9855, H8090, H2665, H-6405, H-4864, H-4766, H2758, H3845, H-3424, H-6022, H-1964, H-4585, H-3022, H-2926, H-9195, H-5035, H-2698, and H-3775.

Cyclooctane, CDN Isotopes, Material Safety Data Sheet, Sheet No. 3440.

Endopeptidases, General Practice Notebook.

Isopropyl Myristate, RITA Your Source for Specialty Chemicals.

Isopropyl Myristate, ChemExper Chemical Directory, Catalog of Chemicals and Suppliers.

Lauric acid sodium salt, RN: 629-25-4.

Limonene, International Programme On Chemical Safety, Concise International Chemical Assessment Document No. 5.

Lyso PC, Cayman Chemical.

The Merck Index, An Encyclopedia of Chemicals, Drugs, and Biologicals, Twelfth Edition, p. 128, 551, 813, 814, 938, 1302, 1308, and 1483.

Mono Decanoyl Octanoyl Glyceride, HUDONG Household Auxiliaries.

N-Decanoic Acid Sodium Salt MSDS, Material Safety Data Sheet, Science Lab.com.

Nonoxynol-9, Wikipedia the free encyclopedia.

Phosphatidylcholine, PDR Health.

Polidocanol (Thesit), Roche Applied Science 2005/2005.

Polysorbate 80, Ingredients, Chemical Formula.

Preparation of Food Contact Notifications and Food Additive Petitions for Food Contact Substances: Chemistry Recommendations, U.S. Food and Drug Administration, CFSAN/Office of Food Additive Safety, Apr. 2002.

Safety (MSDS) Data for Lauric Acid Sodium Salt.

Sodium Glycocholate MSDS, Material Safety Data Sheet, Science Lab.com.

Sodium Myristate, Viva.

Sodium Sulfide, $Na_2S$ $9H_2O$, Reagent Grade, ACS Specifications, Processing KODAK Motion Picture Films, Module 4.

Sodium Sulfide, Material Safety Data Sheet, MSDS No. S5042.

Sodium Taurocholate MSDS, Material Safety Data Sheet, Science Lab.com.

Taurine, Substance Summary, National Library of Medicine, PubChem.

Taurine (2-Aminoethylsulfonic Acid), Changshu Jincheng Chemical Factory, Jincheng Chemicals.

Taurocholic Acid, The Comparative Toxicogenomics Database.

The Safety of Sporanox Capsules and Lamisil Tablets For the Treatment of Onychomycosis, FDA Public Health Advisory, CDER, Drug Information.

Topical Formulation Optimisation For Perungual Drug Delivery, MedPharm.

Universal Preserv-A-Chem, Inc., Products.

Urea, Material Safety Data Sheet According to 91/155 EEC, Promega.

Ursodeoxycholic Acid, The Comparative Toxicogenomics Database.

* cited by examiner

Figure 1:
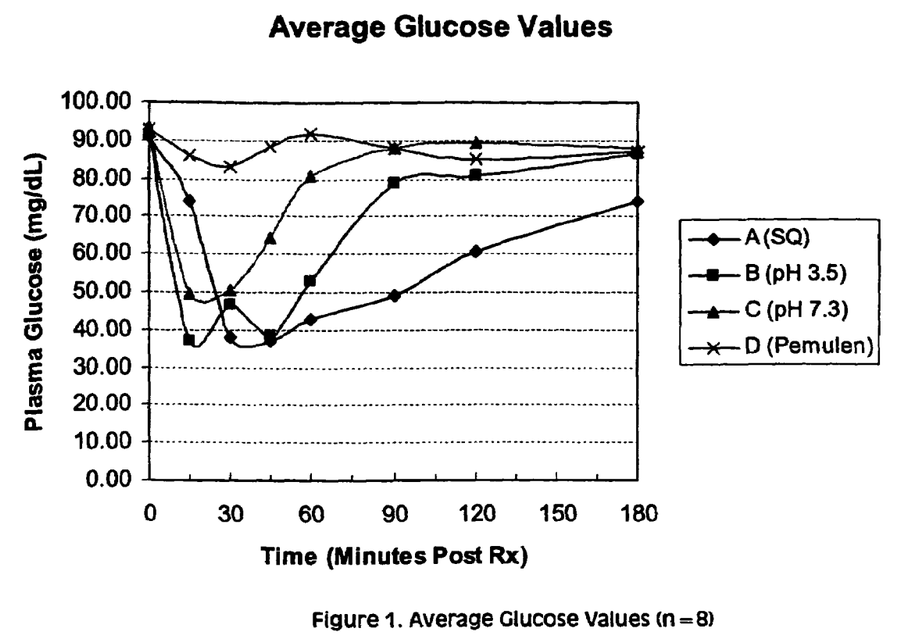

Figure 1. Average Glucose Values (n = 8)

Figure 2:
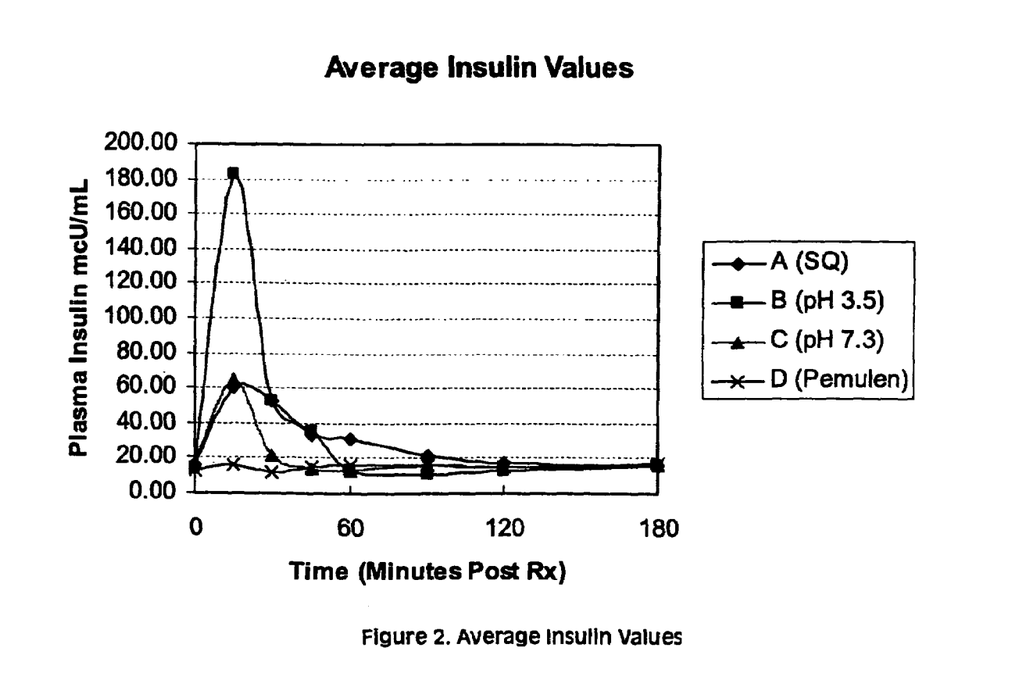

Figure 2. Average Insulin Values

PHARMACEUTICAL COMPOSITIONS AND METHODS FOR INSULIN TREATMENT

This application claims the priority of U.S. Provisional Application Ser. No. 60/527,728 filed on Dec. 8, 2003, the disclosures of which are hereby incorporated by reference in their entireties.

This invention relates to compositions and methods for delivery of insulin, and more particularly for the delivery of insulin other than by injection, across skin, membranes of various body cavities such as ocular, nasal, oral, buccal, anal, rectal, vaginal, and blood brain barrier and like membranes.

Insulin is generally used to treat patients that suffer from diabetes. In general, insulin is delivered to a patient by injection.

U.S. Pat. No. 5,023,252 describes a composition for delivery of insulin by a route other than by injection. More particularly, such patent describes the use of compositions that include permeation enhancers for delivery of insulin through skin and membranes of body cavities without requiring an injection.

The present invention is directed to an improvement in such compositions and the use thereof.

In accordance with the invention, there is provided a pharmaceutical composition comprising: (A) insulin; (B) a permeation enhancer; and (C) a liquid carrier wherein the composition is at an acidic pH.

Applicant has found that when using a composition that contains a combination of insulin and permeation enhancer, improved results are obtained when the composition is at an acidic pH.

The invention further relates to treating a patient in need of insulin with a combination of insulin, a permeation enhancer, and a liquid carrier; the combination having an acidic pH of no greater than 4.5. Preferably the pH of the composition is no greater than 4 nor below 2. The pH is preferably at least 2.

In general, the pH of the composition is at least 2 and no greater than 4.5. In a preferred embodiment, the pH is no greater than 4. A preferred range of pH is from 2.5 to 3.8. In one preferred embodiment the pH is about 3.

The pH of the composition may be maintained by the use of a suitable buffer. The selection of a buffer to maintain the desired pH is deemed to be within the scope of those skilled in the art based on the teachings set forth herein. As representative examples of suitable buffers there may be mentioned citric acid buffer, phosphate buffer, and the like, as is in common use and also suitable for medical formulations.

In general, the permeation enhancer that is employed is one that enhances the permeation of the insulin composition through the membrane of a bodycavity In general, the permeation enhancer that is employed is one that enhances the permeation of the insulin composition through the membrane of a body cavity and in particular through the nasal mucosa.

In a composition containing an effective amount of insulin a preferred permeation enhancer is a compound of the structure:

wherein X and Y are oxygen, sulfur or an imino group of the structure or =N—R with the proviso that when Y is the imino group, X is an imino group, and when Y is sulfur, X is sulfur or an imino group, A is a group having the structure wherein X and Y are defined above, m and n are integers having a value from 1 to 20 and the sum of m+n is not greater than 25, p is an integer having a value of 0 or 1, q is an integer having a value of 0 or 1, r is an integer having a value of 0 or 1, and each of R, $R_1$, $R_2$, $R_3$, $R_4$, $R_5$ and $R_6$ is independently hydrogen or an alkyl group having from 1 to 6 carbon atoms which may be straight chained or branched provided that only one of $R_1$ to $R_6$ can be an alkyl group, with the proviso that when p, q and r have a value of 0 and Y is oxygen, m+n is at least 11, and with the further proviso that when X is an imino group, q is equal to 1, Y is oxygen, and p and r are 0, then m+n is at least 11, and said compound will enhance the rate of the passage of the drug across body membranes. Hereinafter these compounds are referred to as enhancers. When R, $R_1$, $R_2$, $R_3$, $R_4$, $R_5$ or $R_6$ is alkyl it may be methyl, ethyl, propyl, isopropyl, butyl, isobutyl, sec-butyl, amyl, hexyl, and the like. Such permeation enhancers are described in U.S. Pat. No. 5,023,252 and U.S. Pat. No. 5,731,303.

Preferably, the compounds of this invention are the cyclic lactones (the compounds wherein both X and Y are oxygen, (q is 1 and r is 0), the cyclic diesters (the compounds wherein both X and Y are oxygen, and both q and r are 1), and the cyclic ketones (the compounds wherein both q and r are 0 and Y is oxygen). In the cyclic diesters m+n is preferably at least 3. In the cyclic ketones m+n is preferably from 11 to 15 and p is preferably 0.

Enhancers of the above structural formula are referred to herein as "Hsieh enhancers" and are described, for example, in aforementioned U.S. Pat. Nos. 5,023,252 and 5,731,303 (hereinafter "Hsieh Patents"). Such enhancers are lipophilic and are "membrane-compatible," meaning that they do not cause damage to the membrane on which the composition of the present invention is to be applied (hereinafter "target membrane"). Such enhancers produce also a low level of irritability or no irritability to the target membrane and, in fact serve as an emollient.

Preferred enhancers for use in the present invention are macrocyclic enhancers. The term "macrocyclic" is used herein to refer to cyclic compounds having at least 12 carbons in the ring. Examples of preferred macrocyclic enhancers for use in the present invention include: (A) macrocyclic ketones, for example, 3 methylcyclopentadecanone (muscone), 9-cycloheptadecen-1-one (civetone), cyclohexadecanone, and cyclopentadecanone (normuscone); and (B) macrocyclic esters, for example, pentadecalactones such as oxacyclohexadecan-2-one (cyclopentadecanolide, ω-pentadecalactone).

Oxacyclohexadecan-2-one and cyclopentadecanone are especially preferred.

Although the above are preferred permeation enhancers, one of ordinary skill in the art would recognize that the instant teachings would also be applicable to other permeation enhancers. Non-limiting examples of other permeation enhancers useful in the instant invention are the simple long chain esters that are Generally Recognized As Safe (GRAS) in the various pharmacopoeial compendia. These may include simple aliphatic, unsaturated or saturated (but preferably fully saturated) esters, which contain up to medium length chains. Non-limiting examples of such esters include isopropyl myristate, isopropyl palmitate, myristyl myristate, octyl palmitate, and the like. The enhancers are of a type that are suitable for use in a pharmaceutical composition. The artisan of ordinary skill will also appreciate that those materials that are incompatible with or irritating to mucous membranes should be avoided.

The enhancer is present in the composition in a concentration effective to enhance penetration of the insulin, to be delivered, through the membrane. Various considerations should be taken into account in determining the amount of enhancer to use. Such considerations include, for example, the amount of flux (rate of passage through the membrane) achieved and the stability and compatibility of the components in the formulations. The enhancer is generally used in an amount of about 0.01 to about 25 wt. % the composition, more generally in an amount of about 0.1 to about 15 wt. % the composition, and in preferred embodiments in an amount of about 0.5 to about 15 wt % the composition.

The liquid carrier is present in the composition in a concentration effective to serve as a suitable vehicle for the compositions of the present invention. In general, the carrier is used in an amount of about 40 to about 98 wt. % of the composition and in preferred embodiments in an amount of about 50 to about 98 wt. % of the composition.

The insulin compositions of the present invention are preferably delivered as a nasal spray. In such an embodiment, the preferred liquid carrier is water with the insulin being dispersed or dissolved in the water in a therapeutically effective amount.

In one preferred embodiment, the permeation enhancer is emulsified in the aqueous phase that contains the insulin. The emulsification may be effected through the use of one or more suitable surfactants. The selection of a suitable surfactant is deemed to be within the scope of those skilled in the art based on the teachings herein. Essentially any suitable surfactant or mixture of surfactants can be used in the practice of the present invention, including, for example, anionic, cationic, and non-ionic surfactants. Preferred surfactants are non-ionic surfactants, with those having a hydrophilic-lipophilic balance (HLB) of from about 7 to about 14 being particularly preferred. Examples of such non-ionic surfactants are PEG-60 corn glycerides, PEG-20 sorbitan monostearate, phenoxy-poly(ethyleneoxy)ethanol, sorbitan monooleate, and the like. Especially preferred are compendial surfactants such as those described in compendia such as the Food Chemicals Codex, National Formulary, U.S. Pharmacopeia, and the Code of Federal Regulations. It is preferred that the average diameter of the droplets of the emulsion be from about 500 mn to about 20 µm and more preferably from about 1 µm to about 10 µm. In general the surfactant is present in an amount no greater than about 2 wt. % the composition and more generally no greater than about 0.5 wt. % the composition.

In one preferred embodiment, the emulsified or discontinuous phase that contains the permeation enhancer is in the form of droplets. In general, smaller droplets confer greater stability. Larger droplets may cause instability and decrease shelf-life. In preferred embodiments the droplet size ranges from 0.1 microns to 20 microns and preferably from 0.1 microns to 5 microns.

In general compositions that contain insulin are stored in a refrigerator and such refrigeration may result in crystallization of the permeation enhancer. In order to inhibit or prevent such crystallization, in a preferred embodiment the composition includes one or more crystallization inhibitors to inhibit the crystallization of the permeation enhancer. Crystallization, if allowed to proceed, renders the emulsion unstable and has an adverse effect on shelf life. Preferred crystallization inhibitors function by lowering the temperature at which the involved compound crystallizes. Examples of such crystallization inhibitors include natural oils, oily substances, waxes, esters, and hydrocarbons. Examples of natural oils or oily substances include Vitamin E acetate, octyl palmitate, sesame oil, soybean oil, safflower oil, avocado oil, palm oil, and cottonseed oil. The selection of a suitable crystallization inhibitor is deemed to be within the scope of those skilled in the art from the teachings herein. Preferred crystallization inhibitors function by lowering the temperature at which the permeation enhancer crystallizes.

Inhibitors which are capable of lowering the temperature of crystallization of the involved compound to below about 25° C. are particularly preferred, with those capable of lowering the crystallization of the involved compound to below about 5° C. being especially preferred. Examples of especially preferred crystallization inhibitors for use in inhibiting the crystallization of oxacyclohexadecan-2-one include hexadecane, isopropyl myristate, octyl palmitate, cottonseed oil, safflower oil, and Vitamin E acetate, each of which may be used in pharmaceutical preparations.

The crystallization inhibitor is present in the composition in a concentration effective to inhibit the crystallization of the permeation enhancer. In general the crystallization inhibitor is present in an amount of about 0.001 to about 5 wt. % the composition, more generally in an amount of from about 0.01 to about 2 wt % the composition. In one embodiment the crystallization inhibitor is present in an amount of from about 0.1 to about 1 wt. % of the composition. The crystallization inhibitor is one preferably used when the enhancer has a crystallization temperature above about 0 degrees Centigrade. In particular, for example, a crystallization inhibitor is preferably used when the enhancer is, pentadecalactone and/or cyclohexadecanone, since these crystallize above room temperature.

The composition of the present invention is generally delivered through a nasal spray applicator. If intra-nasal application is desired, the composition may be placed in an intra-nasal spray-dosing device or atomizer and be applied by spraying it into the nostrils of a patient for delivery to the mucous membrane of the nostrils. A sufficient amount is applied to achieve the desired systemic or localized drug levels. For an intra-nasal spray, up to about 200 microliters is typically applied, with an application of about 50 to about 150 microliters being preferred. One or more nostrils may be dosed and application may occur as often as desired or as often as is necessary. In preferred embodiments, the nasal spray applicator is selected to provide droplets of the composition of a mean size of from about 10 microns to about 200 microns. More generally the droplet size is from about 30 microns to about 100 microns.

The insulin spray composition of the invention is generally employed in a dosing regimen that is dependent on the patient being treated. Thus the frequency of the use and the amount of the dose may vary from patient to patient. In general, dosing is in an amount (the amount internalized after absorption from the mucosa) of from about 3 IU to about 15 IU and the frequency of dose is 3 to 4 times per day. As known in the art, the treatment of a disease such as diabetes through insulin therapy varies from patient to patient, and based on known insulin therapy and the teachings herein one skilled in the art can select the dosing regimen and dosage for a particular patient or patients.

The composition of the present invention comprises insulin. The insulin is present in the composition in a therapeutically-effective amount. In general the insulin is present in an amount of about 0.01 to about 15 wt. % of the composition, more generally an amount of about 0.01 to about 10 wt. % of the composition. In one embodiment the insulin is present in an amount of about 0.1 to about 5 wt. % of the composition.

Although a preferred embodiment is a preformulated composition, it is also within the scope of the present invention that a patient may be treated with the hereinabove described combination that is not preformulated; i.e., the insulin in liquid carrier and the enhancer may be mixed at the time of application, such as where the mixing occurs in an atomizer at the time the composition is sprayed.

The Examples illustrate preferred embodiments of the invention and are not to be regarded as limiting.

EXAMPLE 1

Four separate aqueuos insulin emulsions of the present invention (formulations A, B, C, and D) are prepared according to the formulations described in the table below. Component CPE-215 is the Applicant's proprietary compound and is also known as Cyclopentadecanolide; it facilitates the migration of insulin through the nasal mucosa.

Insulin Formulation for Pig Experiment

| | Code: | | | |
|---|---|---|---|---|
| | A | B | C | D |
| Reagents: | | | | |
| | % | % | % | % |
| Insulin | 0.1 | 1.0 | 1.0 | 1.0 |
| CPE-215 | — | 2.0 | 2.0 | 2.0 |
| Cottonseed Oil | — | 1.0 | 1.0 | 0.7 |
| Glycerin | — | — | — | 2.0 |
| Sorbitan Laurate (a.k.a. Crill 1; a surfactant) | — | 0.6 | 0.6 | — |
| Polysorbate 20 (a.k.a. Crillet 1; a surfactant) | — | 0.7 | 0.7 | — |
| Pemulen TR2 | — | — | — | 0.1 |
| H2O | 99.1 | 94.3 | 93.2 | 93.7 |
| TEA | — | — | — | 0.5 |
| HCl (5 N) | — | — | 0.2 | — |
| NaOH (1 N) | — | — | 1.3 | — |
| Citric Acid (1 H2O) | 0.6 | 0.3 | — | — |
| Sodium Citrate (2 H2O) | 0.2 | 0.1 | — | — |
| Benzalkonium chloride | — | — | — | 0.003 |
| | 100 | 100 | 100 | 100 |
| pH: | 3.19 | 3.53 | 7.32 | 8.07 |

EXAMPLE 2

C-peptide blood levels can indicate whether or not a person is producing insulin and approximately how much. Insulin is initially synthesized in the pancreas as proinsulin. In this form the alpha and beta chains of active insulin are linked by a third polypeptide chain called the connecting peptide, or C-peptide, for short. Because both insulin and C-peptide molecules are secreted, for every molecule of insulin in the blood, there is one of C-peptide. Therefore, levels of C-peptide in the blood can be measured and used as an indicator of insulin production in those cases where exogenous insulin (from injection) is present and mixed with endogenous insulin (that produced by the body) a situation that would make meaningless a measurement of insulin itself. The C-peptide test can also be used to help assess if high blood glucose is due to reduced insulin production or to reduced glucose intake by the cells. There is little or no C-peptide in the blood of type 1 diabetic humans, and C-peptide levels in type 2 diabetics can be reduced or normal. The concentrations of C-peptide in non-diabetics are on the order of 0.5–3.0 ng/ml.

An evaluation of the compositions of this invention was carried out in vivo as described below.

Pharmacokinetics and Pharmacodynamics in Yucatan Minipigs of Intranasal CPE-215/Insulin Formulations This study was performed in accordance with the NIH "Guide For the Care and Use of Laboratory Animals" and the Federal Animal Welfare Act, and followed a protocol approved by the University of New Hampshire Institutional Animal Care and Use Committee. This study's objective was to evaluate and characterize the pharmacokinetic and pharmacodynamic effectiveness of insulin formulations after intranasal delivery to Yucatan minipigs.

Previously, it had been determined, in beagles (Hseih, 1993), that Cyclopentadecanolide facilitates the migration of insulin through the nasal mucosa. In order to verify this in minipigs, as a step toward evaluation in human volunteers, formulations were assessed for insulin blood levels and glucodynamics.

Materials Methods, and Formulations

The formulations tested were aqueous insulin emulsions, containing pharmaceutical grade human recombinant insulin, obtained from Diosynth, Inc., a division of Akzo Nobel, Inc. These formulations varied slightly in composition; however, each contained insulin at 1% w/w, and CPE-215 at 2% w/w. These formulations were dispensed from intranasal atomizers, developed for humans by Valois of America. Two puffs of 100 microliters each were dispensed to pigs that had previously been cannulated with an indwelling jugular catheter. Each 100 microliter spray dispensed 1 milligram, or approximately 25 IU of insulin. An extension to the actuator was used, provided also by Valois of America, the need for which (to deliver formulation to the absorptive surface of the vestibule and labyrinthine turbinate region) was determined in a preliminary pilot study. The same actuator, dispensing 100 microliters, was used with the extension attached. These intranasally delivered doses were compared to three units of insulin administered subcutaneously (SQ) as a positive control.

Animal Protocol

Four female Yucatan miniature swine (pigs) were purchased from the UNH Miniature Swine Research Farm. During the study, the pigs were housed in an environmentally controlled research animal room (temperature 25+/−2C and 12 hour light/dark cycle), fed commercial research pig chow, and had free access to water at all times. The pigs were 21 week-old Yucatan females:

Pig #1, Tag 121-5; Weight at start of study: 16.8 kg; DOB Nov. 26, 2002

Pig #2, Tag 121-4; Weight at start of study: 22.3 kg; DOB Nov. 26, 2002 (Note: #1 and #2 are littermates]

Pig #3, Tag 122-7; Weight at start of study: 18.3 kg; DOB Dec. 1, 2002

Pig #4, Tag 122-9; Weight at start of study: 15.5 kg; DOB Dec. 1, 2002 [Note: #3 and #4 are littermates].

Catheterization Methodology

The animals were prepared for the study with the surgical implantation of a jugular catheter 4 to 6 days before the study start. After heavy sedation with an intramuscular dose of xylazine and ketamine, the animals were masked down and maintained to effect deep surgical anesthesia with inhalation of isofluorane anesthetic and oxygen. With the animals in dorsal recumbency, a skin incision was made in the right jugular furrow and followed by blunt dissection to expose the subcutaneous and perivascular connective tissues to expose the right jugular vein cranial to the thoracic inlet. A length of 0.050 inch bore Tygon® intravenous catheter tubing was inserted through a small incision in the clamped vein and positioned caudally into the anterior vena cava (approximately 12 to 15 cm from the jugular incision). The catheter was transfixed to the vein and deep subcutaneous tissues suture. The jugular vein cranial to the catheter was ligated with polypropylene suture. The free end of the catheter was routed by blunt dissection through the subcutis to the interscapular dorsum, pulled through a small skin incision, and transfixed to the skin with polypropylene suture. The catheter was capped with a syringe docking device and filled with an anti-thrombotic preparation. The antithrombotic consisted of 60% (w/v) polyvinylpyrrolidone (10,000 mw, PVP-10) and physiologic saline/sodium heparin (50,000 units of heparin per 100 mL). The subcutis and skin incision in the jugular furrow were closed with synthetic absorbable and polypropylene sutures, respectively. The animals were comfortably bandaged to protect the catheter and skin incision and covered with a vest made for dog catheter work. Intramuscular butorphanol was administered as an analgesic immediately and 12 hours after surgery.

Study Design

At the time of dosing, the pigs were restrained in a cloth sling. The pigs were afterwards free to move about their respective individual pens and were only temporarily restrained in close quarters at the front of the pen with a movable wooden gate at the time of blood sampling. Each pig was dosed twice with each of the four different formulations over a two week period with at least 18 hours between treatments. The intranasal dosing (Formulation B, C, D) entailed dispensing 100 µL of a 1% insulin emulsion through an aerosol doser (human type intranasal actuator), once per each nostril (Total dose 50 IU), or subcutaneous dosing (Formulation A), 120 0 µL of a 0.1% buffered sterile solution using a 1 cc sterile syringe (3 IU) equipped with a 22 ga. needle. Dosing intervals between pigs was timed, and was approximately five minutes.

Baseline venous blood specimens were collected just prior to intranasal or SQ insulin administration, and blood was thereafter sampled at 0 (just before treatment), 15, 30, 45, 60, 90, 120, and 180 minutes after application. Bleeding was approximately five minutes apart between pigs, the interval adjusted relative to the dosing time within one minute of target time. Each pig was monitored with a hand-held commercial glucometer at each blood collection time to ensure animal wellness.

The blood was collected into sodium heparinized glass tubes. The plasma was retrieved and stored at −20° C. until analyzed for insulin, C-peptide, and glucose. There were eight days of treatment, with each of the four pigs treated each day. Pigs were crossed over (two successive identical latin squares) with each pig receiving a different treatment each day, according to the following schedule:

Treatment Schedule

| D = Day | P = Pig | Treatments |
| --- | --- | --- |
| D1 = Mar. 25, 2003 | P1 = Pig 121-5 | A = Subcutaneous 120 µL (3 IU) |
| D2 = Mar. 26, 2003 | P2 = Pig 121-4 | B = IN Form. 013-44-2 pH 3.5 |
| D3 = Mar. 27, 2003 | P3 = Pig 122-7 | C = IN Form. 013-44-3 pH 7.32 |
| D4 = Mar. 28, 2003 | P4 = Pig 122-9 | D = IN Form. 013-45 pH 8.0 |
| D5 = Apr. 1, 2003 | | |
| D6 = Apr. 2, 2003 | | |
| D7 = Apr. 3, 2003 | | |
| D8 = Apr. 4, 2003 | | |

Treatments/Days

| Day | Pig 1 | Pig 2 | Pig 3 | Pig 4 |
| --- | --- | --- | --- | --- |
| 1 | A | B | C | D |
| 2 | B | C | D | A |
| 3 | C | D | A | B |
| 4 | D | A | B | C |
| 5 | A | B | C | D |
| 6 | B | C | D | A |
| 7 | C | D | A | B |
| 8 | D | A | B | C |

Sample Collection and Assay Methods

Heparinized plasma was analyzed for insulin concentration using a commercial RIA assay for insulin (Linco research, Inc.; Human Insulin Specific RIS Kit, Cat# HI-14K). Insulin was reported in micro International Units/milliliter of plasma (µU/mL). C-Peptide was analyzed with a commercial kit specific for porcine C-Peptide (Linco research, Inc.; Porcine C-Peptide RIA Kit, Cat# PCP-22K) and reported in units of ng/mL.

Glucose was measured at the time of collection using a Glucometer (Lifescan (J&J) One Touch Fast Take™), and in the laboratory using a commercial enzymatic assay (Sigma Diagnostics, Procedure 315) and was measured in mg/dL.

Deviation from Protocol

There were no deviations from protocol.

Results for Glucose

The results showed good reduction in blood glucose values, as measured in blood by the hexokinase enzymatic method, and are historically commensurate for this positive control, SQ insulin; the SQ dose reached a minimum glucose level at an average of 30 minutes Post Rx. For intranasal Formulation B, excellent glucodynamic reduction was seen with a more rapid onset, 15 minutes or faster to trough, but of shorter duration (90–120 min.) than SQ (180 min.). Formulation C had a similar rapid onset to B, but of less magnitude. Formulation D was devoid of appreciable glucodynamic activity. The reproducibility, both intradose and day to day, was good (no variances of any treatment differed significantly, P<0.05). (See FIG. 1)

The enzymatic glucose assay correlated well with the corresponding glucometer results performed at the time of blood collection (r=0.9575; p<0.0001).

Results for Insulin

The results showed good insulin blood levels for the Formulation A, SQ positive control, with the average value peaking at 15 minutes with an average $C_{max}$ of 59.85 µU/mL. (See FIG. 2).

Formulation B showed much higher blood levels than any other formulation, peaking at 15 minutes with an average $C_{max}$ of 182.4 µU/mL. (See FIG. 2).

Formulation C showed lower blood levels than either A or B, indicating reduced delivery of insulin at physiological pH compared with the acidic form, having a $C_{max}$ of 64.59 µU/mL at 15 minutes. (See FIG. 2).

Formulation D showed little change over fasted baseline levels. No $C_{max}$ was observed. (See FIG. 2).

Results for C-Peptide

C-Peptide for fasted, untreated animals (time zero) averaged 0.35 ng/mL (n=36). The onset of action of the four treatments was similar to the respective curves obtained for the glucodynamics. Treatment B has a faster onset of depression of C-Peptide, followed by A, then C, then D. Treatment A had the longest depression of C-Peptide, approximately 3 hours, whereas the other treatments had normal levels by this time, reflecting resumption of endogenous insulin production.

We claim:

1. A pharmaceutical composition in a form suitable for nasal delivery to a patient comprising: a therapeutically effective amount of insulin, a permeation enhancer, and a liquid carrier; said composition being at an acidic pH, but no greater than a pH of 4.5, and said permeation enhancer being a Hsieh enhancer having the following structure:

wherein X and Y are oxygen, sulfur or an imino group of the structure or =N—R with the proviso that when Y is the imino group, X is an imino group, and when Y is sulfur, X is sulfur or an imino group, A is a group having the structure wherein X and Y are defined above, m and n are integers having a value from 1 to 20 and the sum of m+n is not greater than 25, p is an integer having a value of 0 or 1, q is an integer having a value of 0 or 1, r is an integer having a value of 0 or 1, and each of R, $R_1$, $R_2$, $R_3$, $R_4$, $R_5$ and $R_6$ is independently hydrogen or an alkyl group having from 1 to 6 carbon atoms which may be straight chained or branched provided that only one of $R_1$ to $R_6$ can be an alkyl group, with the proviso that when p, q and r have a value of 0 and Y is oxygen, m+n is at least 11, and with the further proviso that when X is an imino group, q is equal to 1, Y is oxygen, and p and r are 0, then m+n is at least 11.

2. The pharmaceutical composition of claim 1, wherein said acidic pH is from about 2 to about 4.

3. The pharmaceutical composition of claim 1, wherein said acidic pH is about 3.

4. The pharmaceutical composition of claim 1, wherein said acidic pH is about 3.5

5. The pharmaceutical composition of claim 1, further comprising a crystallization inhibitor.

6. The pharmaceutical composition of claim 1, wherein said composition is in the form of an emulsion.

7. The pharmaceutical composition of claim 1, wherein said composition is in the form of a spray emulsion.

8. The pharmaceutical composition of claim 1, wherein said Hsieh enhancer is cyclopentadecalactone or cyclohexadecanone.

9. A method for treating a patient in need of insulin comprising treating said patient by nasally administering to said patient a pharmaceutical composition in a form suitable for nasal delivery to a patient comprising: a therapeutically effective amount of insulin, a permeation enhancer, and a liquid carrier; said composition being at an acidic pH, but no greater than a pH of 4.5, and said permeation enhancer being a Hsieh enhancer having the following structure:

wherein X and Y are oxygen, sulfur or an imino group of the structure or =N—R with the proviso that when Y is the imino group, X is an imino group, and when Y is sulfur, X is sulfur or an imino group, A is a group having the structure wherein X and Y are defined above, m and n are integers having a value from 1 to 20 and the sum of m+n is not greater than 25, p is an integer having a value of 0 or 1, q is an integer having a value of 0 or 1, r is an integer having a value of 0 or 1, and each of R, $R_1$, $R_2$, $R_3$, $R_4$, $R_5$ and $R_6$ is independently hydrogen or an alkyl group having from 1 to 6 carbon atoms which may be straight chained or branched provided that only one of $R_1$ to $R_6$ can be an alkyl group, with the proviso that when p, q and r have a value of 0 and Y is oxygen, m+n is at least 11, and with the further proviso that when X is an imino group, q is equal to 1, Y is oxygen, and p and r are 0, then m+n is at least 11.

10. The method of claim 9, wherein said acidic pH is from about 2 to about 4.

11. The method of claim 9, wherein said acidic pH is about 3.

12. The method of claim 9, wherein said acidic pH is about 3.5

13. The method of claim 9, wherein said composition further comprises a crystallization inhibitor.

14. The method of claim 9, wherein said composition is in the form of an emulsion.

15. The method of claim 9, wherein said composition is in the form of a spray emulsion.

16. The method of claim 9, wherein said Hsieh enhancer is cyolopentadecalactone or cyclohexadecanone.

17. A product including the pharmaceutical composition of claim 1, wherein said pharmaceutical composition is contained in, and deliverable from, an applicator selected from the group consisting of: nasal spray applicators, intranasal spray-dosing devices, and atomizers.

18. A method of treating a patient in need of insulin treatment comprising: using the product of claim 17 to effect a delivery of said pharmaceutical composition to the nasal mucosa of said patient.

19. The method claim 18, wherein said delivery is up to about 200 microliters.

20. The method claim 18, wherein said delivery is between about 50 to about 150 microliters.

21. The pharmaceutical composition of claim 1, wherein said permeation Hsieh enhancer is a macrocyclic permeation enhancer.

22. The pharmaceutical composition of claim 21, wherein said macrocyclic permeation enhancer is cyclopentadecanolide.

23. A pharmaceutical composition in a form suitable for nasal delivery to a patient comprising: an aqueous phase containing a therapeutically effective amount of insulin and a permeation enhancer emulsified in said aqueous phase, said composition being at an acidic pH, but no greater than a pH of 4.5, and said permeation enhancer being a Hsieh enhancer having the following structure:

wherein X and Y are oxygen, sulfur or an imino group of the structure or =N—R with the proviso that when Y is the imimo group, X is an imino group, and when Y is sulfur, X is sulfur or an imino group, A is a group having the structure wherein X and Y are defined above, m and n are integers having a value from 1 to 20 and the sum of m+n is not greater than 25, p is an integer having a value of 0 or 1, q is an integer having a value of 0 or 1, r is an integer having a value of 0 or 1, and each of R, $R_1$, $R_2$, $R_3$, $R_4$, $R_5$ and $R_6$ is independently hydrogen or an alkyl group having from 1 to 6 carbon atoms which may be straight chained or branched provided that only one of $R_1$ to $R_6$ can be an alkyl group, with the proviso that when p, q and r have a value of 0 and Y is oxygen, m+n is at least 11, and with the further proviso that when X is an imino group, q is equal to 1, Y is oxygen, and p and r are 0, then m+n is at least 11.

24. The pharmaceutical composition of claim 23, wherein said Hsieh enhancer is a macrocyclic permeation enhancer.

25. The pharmaceutical composition of claim 24, wherein said macrocyclic permeation enhancer is selected from the group consisting of macrocyclic ketones and macrocyclic esters.

26. The pharmaceutical composition of claim 25, wherein said macrocyclic ketone is selected from the group consisting of 3 methylcyclopentadecanone (muscone), 9-cycloheptadecen-1-one (civetone), cyclohexadecanone, and cyclopentadecanone (normuscone).

27. The pharmaceutical composition of claim 25, wherein said macrocyclic ester is a pentadecalactone.

28. The pharmaceutical composition of claim 27, wherein said pentadecalactone is oxacyclohexadecan-2-one (cyclopentadecanolide, ω-pentadecalactone).

29. The pharmaceutical composition of claim 23, wherein said permeation enhancer is emulsified within said aqueous phase by a surfactant.

30. The pharmaceutical composition of claim 29, wherein said surfactant is selected from the group consisting of: anionic surfactants, cationic surfactants, non-ionic surfactants, and mixtures of the foregoing.

31. The pharmaceutical composition of claim 30, wherein said surfactant is a non-ionic surfactant.

32. The pharmaceutical composition of claim 31, wherein said non-ionic surfactant has a hydrophulic-lipophilic balance (HLB) of from about 7 to about 14.

33. The pharmaceutical composition of claim 23, further comprising a crystallization inhibitor capable of lowering the temperature of crystallization of said permeation enhancer to below about 25° C.

34. The pharmaceutical composition of claim 33, wherein said crystallization inhibitor is capable of lowering the temperature of crystallization of said permeation enhancer to below about 50° C.

35. The pharmaceutical composition of claim 33, wherein said crystallization inhibitor is selected from the group consisting of natural oils, oily substances, waxes, esters, and hydrocarbons.

36. The pharmaceutical composition of claim 35, wherein said crystallization inhibitor is a natural oil.

37. The pharmaceutical composition of claim 36, wherein said natural oil is cottonseed oil.

38. A method for treating a patient in need of insulin comprising treating said patient by nasally administering to said patient a pharmaceutical composition, in a form suitable for nasal delivery to a patient, comprising: an aqueous phase containing a therapeutically effective amount of insulin and a permeation enhancer emulsified in said aqueous phase, said composition being at an acidic pH, but no greater than a pH of 45 and said permeation enhancer being a Haich enhancer having the following structure;

wherein X and Y are oxygen, sulfur or an imino group of the structure or =N—R with the proviso that when Y is the imino group, X is an imino group, and when Y is sulfur, X is sulfur or an imino group, A is a group having the structure wherein X and Y are defined above, m and n are integers having a value from 1 to 20 and the sum of m+n is not greater than 25, p is an Integer having a value of 0 or 1, q is an integer having a value of 0 or 1, r is an integer having a value of 0 or 1, and each of R, $R_1$, $R_2$, $R_3$, $R_4$, $R_5$ and $R_6$ is independently hydrogen or an alkyl group having from 1 to 6 carbon atoms which may be straight chained or branched provided that only one of $R_1$ to $R_6$ can be an alkyl group, with the proviso that when p, q and r have a value of 0 and Y is oxygen, m+n is at least 11, and with the further proviso that when X is an imino group, q is equal to 1, Y is oxygen, and p and r are 0, then m+n is at least 11.

39. The method of claim 38, wherein said permeation enhancer is a macrocyclic Hsieh enhancer.

40. The method of claim 39, wherein said macrocyclic permeation enhancer is selected from the group consisting of macrocyclic ketones and macrocyclic esters.

41. The method of claim 40, wherein said macrocyclic ketone is selected from the group consisting of 3 methyl-cyclopentadecanone (muscone), 9-cycloheptadecen-1-one (civetone), cyclohexadecanone, and cyclopentadecanone (normuscone).

42. The method of claim 40, wherein said macrocyclic ester is a pentadecalactone.

43. The method of claim 42, wherein said pentadecalactone is oxacyclohexadecan-2-one (cyclopentadecanolide, ω-pentadecalactone).

44. The method of claim 38, wherein said permeation enhancer is emulsified within said aqueous phase by a surfactant.

45. The method of claim 44, wherein said surfactant is selected from the group consisting of: anionic surfactants, cationic surfactants, non-ionic surfactants, and mixtures of the foregoing.

46. The method of claim 45, wherein said surfactant is a non-ionic surfactant.

47. The method of claim 46, wherein said non-ionic surfactant has a hydrophilic-lipophilic balance (HLB) of from about 7 to about 14.

48. The method of claim 38, wherein said pharmaceutical composition further comprises a crystallization inhibitor capable of lowering the temperature of crystallization of said permeation enhancer to below about 25° C.

49. The method of claim 48, wherein said crystallization inhibitor is capable of lowering the temperature of crystallization of said permeation enhancer to below about 5° C.

50. The method of claim 48, wherein said crystallization inhibitor is selected from the group consisting of natural oils, oily substances, waxes, esters, and hydrocarbons.

51. The method of claim 50, wherein said crystallization inhibitor is a natural oil.

52. The method of claim 51, wherein said natural oil is cottonseed oil.

53. A product including the pharmaceutical composition of claim 23, wherein said pharmaceutical composition is contained in, and deliverable from, an applicator selected from the group consisting of: nasal spray applicators, intra-nasal spray-dosing devices, and atomizers.

54. A method of treating a patient in need of insulin treatment comprising: using the product of claim 53 to effect a delivery of said pharmaceutical composition to the nasal mucosa of said patient.

55. The method claim 54, wherein said delivery is up to about 200 microliters.

56. The method claim 54, wherein said delivery is between about 50 to about 150 microliters.

57. The pharmaceutical composition of claim 23, wherein said acidic pH is from about 2 to about 4.

58. The pharmaceutical composition of claim 23, wherein said acidic pH is about 3.

59. The pharmaceutical composition of claim 23, wherein said acidic pH is about 3.5.

60. The pharmaceutical composition of claim 23, wherein said Hsieh enhancer is cyclopentadecalactone or cyclohexadecanone.

61. The method of claim 38, wherein said acidic pH is from about 2 to about 4.

62. The method of claim 38, wherein said acidic pH is about 3.

63. The method of claim 38, wherein said acidic pH is about 3.5.

64. The method of claim 38, wherein said Hsieh enhancer is cyclopentadecalactone or cyclohexadecanone.

65. The method of claim 9, wherein said Hsieh enhancer is a macrocyclic permeation enhancer.

66. The method of claim 65, wherein said macrocyclic permeation enhancer is cyclopentadecanolide.

* * * * *